US008110669B2

(12) United States Patent
Yu et al.

(10) Patent No.: US 8,110,669 B2
(45) Date of Patent: Feb. 7, 2012

(54) APPARATUS AND METHODS FOR DETECTING DNA IN BIOLOGICAL SAMPLES

(75) Inventors: Cheung Hoi Yu, Hong Kong (HK); Lok-Ting Lau, Hong Kong (HK); Selma Sau Wah Lin, New Territories (HK); Duncan Ka-Yun Chan, New Territories (HK)

(73) Assignee: Hai Kang Life Corporation Limited, Shau Kei Wan (HK)

( * ) Notice: Subject to any disclaimer, the term of this patent is extended or adjusted under 35 U.S.C. 154(b) by 0 days.

(21) Appl. No.: 13/049,858

(22) Filed: Mar. 16, 2011

(65) Prior Publication Data

US 2011/0165665 A1    Jul. 7, 2011

Related U.S. Application Data

(62) Division of application No. 12/786,178, filed on May 24, 2010, which is a division of application No. 11/599,479, filed on Nov. 15, 2006, now Pat. No. 7,749,705, which is a division of application No. 10/216,928, filed on Aug. 13, 2002, now Pat. No. 7,153,687.

(51) Int. Cl.
    *C07H 21/02*    (2006.01)
    *C07H 21/04*    (2006.01)
(52) U.S. Cl. ..................... 536/23.1; 536/24.3
(58) Field of Classification Search .................. None
    See application file for complete search history.

(56) References Cited

U.S. PATENT DOCUMENTS

| | | | |
|---|---|---|---|
| 5,128,247 | A | 7/1992 | Koller |
| 5,632,957 | A | 5/1997 | Heller et al. |
| 5,849,486 | A | 12/1998 | Heller et al. |
| 6,051,380 | A | 4/2000 | Sosnowski et al. |
| 6,093,370 | A | 7/2000 | Yasuda et al. |
| 6,287,517 | B1 | 9/2001 | Ackley et al. |
| 6,303,338 | B1 | 10/2001 | Ni et al. |
| 6,325,904 | B1 | 12/2001 | Peeters |
| 6,942,970 | B2 | 9/2005 | Isola et al. |
| 2002/0001801 | A1 | 1/2002 | Fan et al. |

FOREIGN PATENT DOCUMENTS

| | | |
|---|---|---|
| EP | 0 391 608 | 10/1990 |
| JP | 2-286100 | 11/1990 |
| JP | 2000-515251 | 11/2000 |
| JP | 2001178470 * | 7/2001 |
| WO | WO 95/12808 | 5/1995 |
| WO | WO 96/01836 | 1/1996 |
| WO | WO 98/10273 | 3/1998 |
| WO | WO 99/02266 | 1/1999 |
| WO | WO 01/51665 | 7/2001 |
| WO | WO 01/73123 | 10/2001 |
| WO | WO 01/83674 | 11/2001 |
| WO | WO 02/18643 | 3/2002 |
| WO | WO 02/46472 | 6/2002 |

OTHER PUBLICATIONS

Laibinis et al. "orthogonal Self-Assembled Monolayers: Alkanethiois on Gold and Alkane Carboxylic Acids on Alumina", Science, vol. 245, Aug. 25, 1989, pp. 845-647.
Sharma, et al, "Albumin adsorption on to aluminium oxide and polyurethane surfaces", Biomaterials 1990, vol. 11 , May, pp. 255-257.
Taton et al.,"Scanometric DNA Array Detection With Nanoparticle Probes", Science, vol. 289, Sep. 8, 2000, pp. 1757-1760.
Nehls et al., "S-300 Gel Matrix Irreversibly Binds Single-Stranded Nucleic Acids", Trends in Genetics, 1993, pp. 336-337 vol. 9(10).
Polysky-Cynkin et al., "Use of DNA Immobilized on Plastic and Agarose Supports to Detect DNA by Sandwich Hybridization", Clinical Chemistry, 1985, pp. 1438-1443, vol. 31(9).
Wang et al. "Magnetically-Induced Solid-State Electrochemical Detection of DNA Hybridization", J. Am. Chem. Soc., 2002, vol. 124, pp. 4208-4209.
Supplementary European Search Report dated Aug. 1, 2007.
Communication pursuant to Article 94(3) EPC issued in European Application No. 03 783 907.3-2402 on May 26, 2008.
Japanese Office Action with the English Language translation mailed Sep. 15, 2009, in corresponding Japanese application No. 2004-526591.
Edman et al., "Electric field directed nucleic acid hybridization on microchips," *Nucleic Acids Research*, 1997, vol. 25, No. 24, pp. 4907-4914, Oxford University Press.

* cited by examiner

*Primary Examiner* — Albert Navarro
(74) *Attorney, Agent, or Firm* — Buchanan Ingersoll & Rooney PC

(57) ABSTRACT

Apparatus and methods are described for detecting target DNA in a biological sample using capture probes and electrically-assisted hybridization. The reaction cell is formed with an attachment surface of aluminum oxide for better thermal and physical properties, and the aluminum oxide surface is coated with anti-DIG antibody to provide a convenient attachment layer for the capture probes allowing their correct orientation, while the capture probes are formed with a DIG-label so that they attach to the surface of the cell through an anti-DIG/DIG linkage.

3 Claims, 5 Drawing Sheets

With capture probe

Before hybridization    After signal formation

Without capture probe

Before hybridization    After signal formation

With target nucleic acid

Before hybridization

After hybridization

Without target nucleic acid

Before hybridization

After hybridization

With target nucleic acid
(undiluted)

With target nucleic acid
(5-fold dilution)

With target nucleic acid
(10-fold diluted)

Without target nucleic acid

APPARATUS AND METHODS FOR DETECTING DNA IN BIOLOGICAL SAMPLES

This is a Divisional of U.S. application No. 12/786,178, filed May 24, 2010 which is a Divisional of U.S. application No. 11/599,479, filed Nov. 15, 2006 (now U.S. Pat. No. 7,749,705, issued Jul. 6, 2010) which is a Divisional of U.S. application No. 10/216,928, filed Aug. 13, 2002 (now U.S. Pat. No. 7,153,687, issued Dec. 26, 2006).

FIELD OF THE INVENTION

This invention relates to apparatus and methods for detecting DNA in biological samples. In particular the present invention relates to novel apparatus for detecting DNA sequences using electrically-assisted nucleic acid hybridization and to methods for optimizing the performance of such apparatus.

BACKGROUND OF THE INVENTION

The use of electrically-assisted nucleic acid hybridization is a known technique in the analysis of biological samples containing DNA, e.g. blood, plasma, urine etc. Conventionally, a chip for DNA detection is formed from one of a variety of materials including glass, silica and metal. On the surface of the chip a number of electrical contacts are formed using known techniques. To detect a particular DNA sequence in a biological sample, capture probes consisting of complementary DNA fragments are attached to the chip surface. If a biological sample contains the target DNA, the target DNA will bind to the complementary DNA fragments by hybridization, and various imaging techniques may be used to detect such hybridization and thus the presence in the sample of the target DNA. By applying an electric current to the capture probes, the hybridization process may be accelerated and thus the detection process is also accelerated. This basic hybridization technique is described, for example, in U.S. Pat. No. 5,849,486.

PRIOR ART

In such devices and techniques, the major issues concerned are the binding of the capture probes to the surface of the chip, and the imaging and visualization of the hybridization when it occurs. Concerning the latter, a traditional method of detection is fluorescence, but more recently Taton et al, ("Science" Vol. 289, 8 Sep. 2000, pp 1757-1760) describes the use of streptavidin-coated gold nanoparticles for detection. In such a technique gold nanoparticles are coated with an oligonucleotide sequence complementary to the target DNA sequence. A solution containing such coated gold nanoparticles is passed over the surface of the chip and gold particles will then bind to any probes to which the target DNA is bound. The gold particles themselves are too small to be detected, but the chip surface may then be incubated with a solution containing silver ions. The silver ions are deposited onto the surface of the gold nanoparticles to form a visible silver layer, which may be detected by conventional imaging apparatus.

Concerning the binding of the capture probes to the chip surface, one difficulty is that the attachment of the DNA oligonucleotides onto a chip surface (e.g. a silicon wafer) is a critical step that is highly sensitive to disturbances in experimental conditions. In particular when an electric current is applied during the electrically assisted hybridization process, electrolysis may occur that can adversely affect subsequent reactions and detection. It is known for example to coat the chip surface with an agarose gel and the DNA oligonucleotides used as capture probes are labeled at one end with biotin and embedded in the agarose layer by virtue of the high affinity interaction between biotin and streptavidin that is dissolved in the agarose prior to the coating of the chip surface.

However, there are a number of problems with using agarose. Firstly it is very difficult to manipulate a molten agarose gel so as to maintain an even coating on the chip. In addition the density and concentration of the agarose gel must be precisely controlled. Thus manufacture of a chip with a suitable agarose layer is very difficult. Furthermore once applied the gel must be kept moist to prevent drying and cracking, and agarose is very unstable and degrades at high temperatures, and so the chip must be refrigerated after application of the agarose layer. The agarose layer is also very delicate and susceptible to mechanical stresses, and thus the storage and transportation of the finished chip is difficult. In any event, the use of an agarose gel does not overcome the potential problems caused by electrolysis.

SUMMARY OF THE INVENTION

According to the present invention there is provided apparatus for detecting target DNA in a biological sample, comprising a substrate formed with at least one reaction cell, wherein said reaction cell includes an aluminum oxide surface for the attachment of DNA capture probes.

By means of this arrangement some of the problems with the prior art are overcome or at least mitigated because aluminum oxide provides a stable attachment surface that is easy to form and to manipulate, facilitates subsequent handling and storage of the apparatus, and which overcomes or at least mitigates the problems with electrolysis.

The aluminum oxide attachment surface may be faulted by oxidation of a previously fanned aluminum layer, or directly, for example by sputtering.

A method of attaching the capture probes to the aluminum oxide layer would increase the convenience of manufacture. An attachment layer adsorbed to the aluminum oxide would perform this function. It is also important to be able to correctly orient the capture probes with respect to the attachment layer. A protein may perform both of these activities. Preferably this protein may be an antibody to a protein used to label the DNA capture probes, so that the capture probes may be linked to the attachment surface through an antibody-protein pair linkage in a defined orientation. Alternatively, however, the surface could be coated with any protein and the capture probes may be labeled with a protein having a high affinity with the first protein, for example streptavidin and/or biotin.

To reduce the background signal, the attachment surface may be coated with a reagent such as albumin, salmon sperm DNA, Ficoll, or other protein.

Viewed from another broad aspect the present invention includes a kit for the detection of target DNA in a biological sample, said kit comprising:
 (a) a substrate including at least one reaction cell, said at least one reaction cell having an aluminum oxide surface,
 (b) a first reagent comprising capture probes including a complementary DNA fragment to said target DNA,
 (c) a buffer solution for receiving said sample,
 (d) a second reagent comprising detection probes including a complementary DNA fragment to said target DNA,
 (e) a solution of streptavidin-coated gold nanoparticles, and a solution containing silver ions.

Viewed from another aspect the present invention also extends to a DNA chip for detecting target DNA in a sample comprising a substrate having an aluminum oxide surface, and a DNA capture probes attached to said aluminum oxide surface.

Viewed from a still further aspect the invention also extends to a method for detecting target DNA in a biological sample, comprising the steps of
- (a) providing a reaction cell formed with an aluminum oxide surface,
- (b) coating said surface with a first protein to facilitate the binding of the second protein that is attached to the capture probe resulting in the correct orientation of said capture probe,
- (c) adding to said cell a solution containing capture probes formed with a DNA sequence complementary to said target DNA and labeled with a second protein having high affinity with said first protein,
- (d) supplying said sample to said cell,
- (e) adding to said cell a solution containing target DNA detection probes formed with a DNA sequence complementary to said target DNA,
- (f) adding to said cell means for generating a detectable signal in a cell where target DNA has been captured by said capture probes and detected by said detection probes, and
- (g) detecting said signal.

BRIEF DESCRIPTION OF THE DRAWINGS

Some embodiments of the present invention will now be described by way of example and with reference to the accompanying drawings, in which:—

DETAILED DESCRIPTION OF PREFERRED EMBODIMENTS

Figure 1:
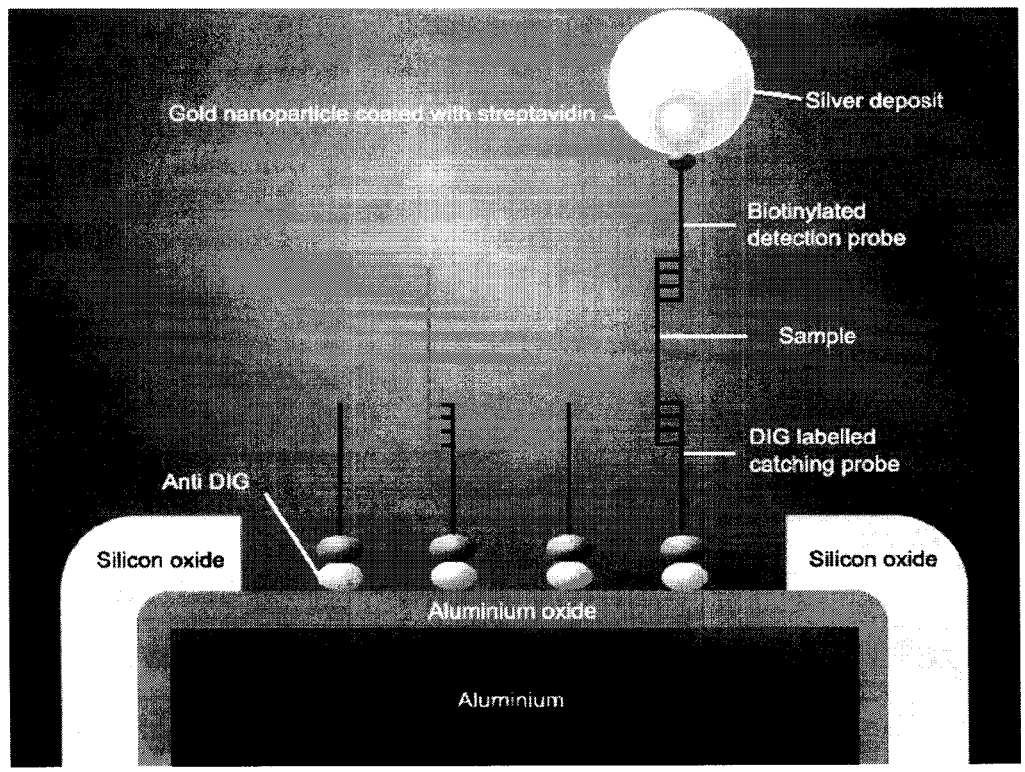
FIG. 1 is a schematic view illustrating a chip according to an embodiment of the invention and also illustrating the hybridization and detection scheme.

Referring firstly to FIG. 1 there is shown schematically a novel apparatus for the detection of DNA in biological samples in accordance with an embodiment of the present invention. The chip comprises a silicon wafer 1 on which a layer 2 of aluminum is fabricated, and a layer of aluminum oxide 3 is foamed on the aluminum layer 2. The aluminum oxide layer 3 is the attachment surface for the DNA probes as will be described below.

The aluminum oxide layer 3 may be formed either by oxidization of the aluminum layer, or by direct deposition of alumina on the surface of the chip without the need for an aluminum layer at all. These possibilities will be now be described in more detail.

In a first method of forming the aluminum oxide layer, aluminum is allowed to grow on a clean aluminum surface that is exposed to oxygen and water. Silica chips that are fabricated with a layer of aluminum on the surface are first rinsed with distilled water, cleaned by dipping into 5% (w/v) NaOH solution for about 30 s, and then washed several times with distilled water according to the technique described in Sharma C P & Sunny M C "Albumin adsorption on to aluminum oxide and polyurethane surfaces" Biomaterials, 1990; 11: 255-257. The chips are then heated overnight at 37° C. in an oven with some water in a container to maintain moisture. Under these conditions the surface of the aluminum oxidizes to alumina with a thickness of about 50 Å. In a modification of this process the chips may be simply cleaned with distilled water and then heated at 60° C. for 48 hours.

As an alternative to forming alumina by oxidation of an aluminum layer, alumina may be deposited directly on a silicon wafer according to the following sputtering conditions:
Equipment: ARC-12M Sputtering system
RF power: 120 W
Base pressure: $1.04 \times 10^{-5}$ torr
Process pressure: $5 \times 10^{-3}$ torr
Gas flow: $Ar/O_2=30.2/7.5$ sccm
Stage rotation: 8 rpm
Sputter time: 45 minutes
Minimum thickness: 100 Å
Chip size: 5 mm×5 mm The alumina-coated chip may be patterned by conventional photolithographic techniques. In addition, whichever method is used to form the alumina layer, prior to hybridization the coated chip is washed once with 1×PBS (phosphate-buffered saline, pH 7.4) at room temperature by pipeting the solution repeatedly over the chip surface. Of the alternative methods of forming the alumina layer, sputtering may be preferred as studies show that is produces the lowest background signal. Whichever technique is used for forming the aluminum layer, the thickness may be at least 50 Å.

Aluminum oxide is preferred for the probe attachment surface because compared with, for example, agarose it is cheaper, more stable and more durable. In addition aluminum oxide can be stored dry and at room temperature. Importantly, aluminum oxide also eliminates the problems associated with electrolysis. In addition, while agarose is difficult to handle to form controlled layers, the pore size and thickness of the alumina layer can easily be controlled (for example by altering the sputtering conditions or the air moisture content). The aluminum oxide can also easily be patterned using conventional photolithographic techniques. The use of a patterned aluminum oxide layer is advantageous because it can reduce the background signal due to reduced non-specific binding, and by increasing the contrast between the area being imaged by the detector and the background.

Referring back to FIG. 1 there is also shown schematically the basic hybridization scheme using an apparatus and method according to an embodiment of the present invention. In particular, in FIG. 1 the attachment surface is a layer of aluminum oxide formed on aluminum. A circular reaction well may be defined by depositing silicon oxide on the aluminum oxide attachment surface. Within each reaction well, capture probes are attached to the aluminum oxide layer. The capture probes are not attached directly, however, but through a linkage formed of digoxigenin (DIG) and anti-digoxigenin (anti-DIG) antibodies. In particular, anti-DIG antibodies are adsorbed by the aluminum oxide surface, and the capture probes are formed with a DIG-label whereby the capture probes may be linked via the anti-DIG antibodies to the aluminum oxide attachment surface. The aluminum oxide surface is very porous and has the ability to bind many different molecules. The anti-DIG coating functions as an attachment layer to ensure that the immobilized DNA capture probes are correctly oriented. If no coating were applied, there is a danger that the detection probe (to be described below) could bind to the aluminum oxide surface and cause interference in the detection of target DNA. In addition, if no coating were applied, the capture probe might bind to the aluminum oxide in the incorrect orientation. In principle, the anti-DIG/DIG linkage could be replaced by any similar pair of compounds, e.g. an antibody and a target protein, or a pair of proteins with very high affinity for each other, or any pair of non-protein molecules that are able to interact with each other. It should also be understood that the order of the antibody/protein or protein/protein linkage could be reversed. For example while in the preferred embodiment described herein anti-DIG is used as the reactivity limiting coating and the capture probes are DIG-labeled this could be reversed. However, in practical terms it is easier to attach a small molecule such as DIG to a capture probe than it would be to attach an antibody to the capture probe. Furthermore it should be noted that the capture probe could be directly attached to the aluminum oxide layer by the addition of a terminal amine or aldehyde group.

It will also be understood that the capture probes are formed with a DNA sequence complementary to the DNA target that is to be detected in a sample. Therefore, when the sample is supplied to the surface of the chip to which the capture probes are attached, if the target DNA is present it will bind to the complementary DNA sequence of the capture probe by the known process of DNA hybridization. The hybridization may preferably be accelerated by the application of an electric current as is known in the art.

Once the sample has been applied to the chip surface, it is then necessary to detect any target DNA from the sample that has become bound to the capture probes. To achieve this a solution containing biotinylated detection probes is added. The detection probes include DNA sequences that are complementary to the target DNA and thus will bind to any target DNA that has previously been caught by the capture probes. To enable the caught target DNA to be visually detected, gold nanoparticles coated with streptavidin are added and because of the affinity of streptavidin with biotin the gold nanoparticles will become attached to the detection probes. The gold nanoparticles themselves are too small to be seen clearly, but a solution containing silver ions may then be added which will be reduced on the surface of the streptavidin-coated gold nanoparticles to faun a silver layer, which is visible as a dark deposit.

To reduce the background signal the chip may preferably be treated with salmon sperm DNA. As an alternative to salmon sperm DNA, albumin, or other proteins, or Ficoll, may be used.

The visibility of the silver deposits may be further enhanced by the use of a fixative solution, such as sodium thiosulfate. Conventional imaging equipment and techniques may then be used to detect dark deposits in the reaction cell, which would result from the presence of the target DNA in the sample.

EXAMPLE

The following example is of a protocol for detecting β-actin DNA in a sample. The hybridization steps are electronically assisted, preferably by pulse hybridization using applied pulses, though continuously applied current is also possible. Pulse hybridization, however, limits damage to the chip and results in a higher signal. Typical hybridization conditions include for the hybridization of the sample DNA to the capture probes the application of 10 second pulses (13 microamps) followed by a 3 second pause repeated for 8 minutes (i.e. a total of 48 pulses. For the hybridization of the detection probe to the captured sample DNA, the same conditions may be used, but for only 3 minutes (i.e. 18 pulses).

1. Anti-DIG is diluted 100-fold with 1× PBS (phosphate-buffered saline), pH 7.4.
2. 50 µl of the diluted anti-DIG is added onto an alumina-coated chip and is incubated at 41° C. for 2 hours.
3. The anti-DIG solution is discarded and the chip is washed 3× with 80 µl 1× PBS, pH 7.4 (pipette up and down during every wash).
4. 1 µl 10 µM of the DIG-labeled capture probes together with 0.2 µg salmon sperm DNA in 50 µl 1× PBS is added onto the chip and incubated at 41° C. for 30 minutes. The salmon sperm DNA is firstly denatured by heating to 95° C. to form single strands and is then mixed with the DIG-labeled capture probes.
5. The DIG-labeled capture probe solution and salmon sperm DNA solution are discarded washed three times with 80 µl 1× PBS and once with 1× SSPE.
6. Add 5 µl 11 µM sample of β-actin sequence (a 91 nucleotide single-stranded target) in 1× SSPE and apply electric pulse current as described for 8 min. After hybridization, wash the chip 3× with 0.1× SSPE.
7. Add detection probe (1 ul, 10 µM) to the chip. Apply electric pulse current as described for 3 min. Wash the chip 3× with 0.1× SSPE and once with 1× PBS.
8. Streptavidin-coated gold nanoparticles (obtained from Sigma Chemical Co., Ltd, St. Louis, Mo., USA) are diluted 10-fold with 1× PBS, pH 7.4.
9. The diluted streptavidin-coated gold nanoparticles are added to the chip surface
10. The diluted streptavidin-coated gold nanoparticle solution is discarded and the chip is washed twice with 80 µl 1× PBS, pH 7.4 (pipette up and down during every wash) and 3× with 80 µl autoclaved milli-Q water (pipette up and down during every wash).
11. A 1:1 mixture of silver enhancer solutions A and B (obtained from Sigma Chemical Co., Ltd, St. Louis, Mo., USA) is prepared just before use and the following steps are performed in a darkroom. 50 µl of the silver enhancer solution is added onto the chip and incubated at room temperature for 5 minutes.
12. The silver enhancer solution is discarded and the chip washed once with autoclaved milli-Q water before 50 µl of 2% sodium thiosulfate is added onto the chip. Pipette up and down once to remove background and to fix the color.
13. Discard the sodium thiosulfate solution after 2 min incubation and washed with 50 µl milli-Q water before 50 µl autoclaved milli-Q water is added onto the chip.
14. Observe the appearance of dark spots on the chip with an optical signal detection system.

Experimental Results

The following experimental results shown in FIGS. 2 to 5 were obtained using the above hybridization protocol with certain parameters being varied as will be understood from the following. In all cases, the basic DNA detection scheme is the following: an aluminum oxide attachment layer provided with anti-DIG, DIG-labeled capture probes having a DNA fragment complementary to a single-stranded nucleic acid target, biotin-labeled detection probes for binding to captured targets, and streptavidin-coated gold nanoparticles with silver enhancement for visualizing detected target DNA.

Figures 2A, 2B:
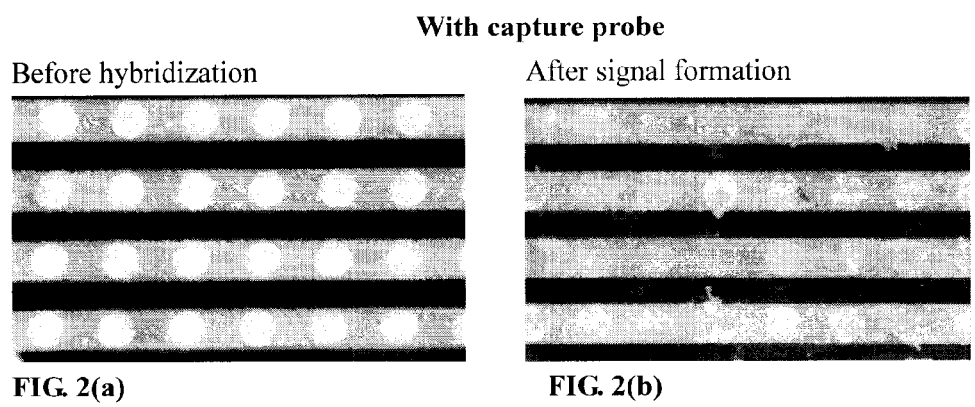
FIGS. 2(a) to (d) show reaction cells obtained experimentally that show that the presence of the capture probe enables the target DNA to be detected.
Figures 2C, 2D:
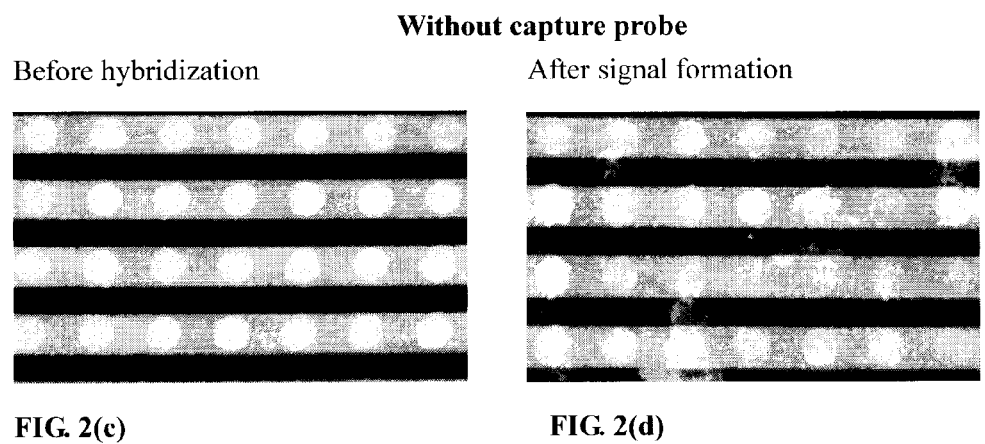
Figure 3A:
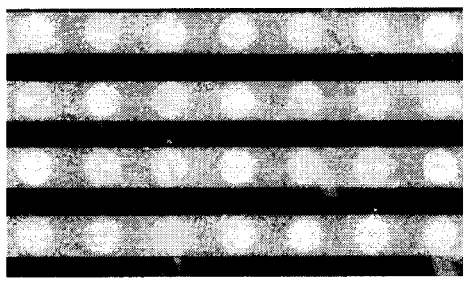
FIGS. 3(a) to (d) show reaction cells obtained experimentally that show that the presence of the target DNA is required before silver deposits will be formed.
Figure 3B:
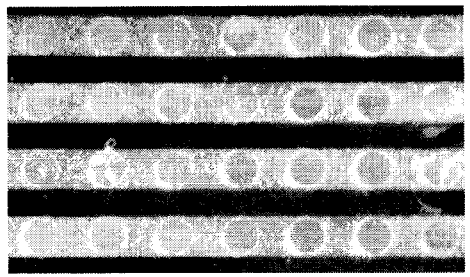
Figure 3C:
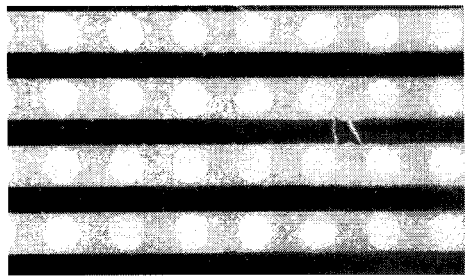
Figure 3D:
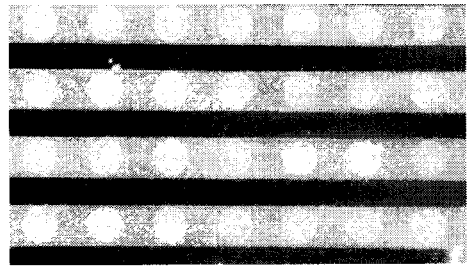

FIGS. 2(a)-(d) illustrate the effectiveness of the DIG-labeled capture probe in the detection of the DNA target. FIGS. 2(a) and (c) both show the chip before hybridization. The reaction cells are white because no silver deposits have been formed. FIGS. 2(b) and (d) show the chip after hybridization with the DIG-labeled capture probe being present in FIG. 2(b) but absent in FIG. 2(d). The reaction cells are seen to be darker in FIG. 2(b) than in FIG. 2(d) showing the deposit of silver.

FIGS. 3(a)-(d) show that darkened silver deposits are only formed in the reaction cells in the presence of the target DNA. Similar to FIG. 2, FIGS. 3(a) and (c) show the chip before hybridization, while FIGS. 3(b) and (d) show the chip after hybridization with the target DNA being present in FIG. 3(b) only and not FIG. 3(d). Again it can be seen that dark deposits of silver are formed in the reaction cells only in the case of FIG. 3(b) where the target DNA is present.

Figure 4A:
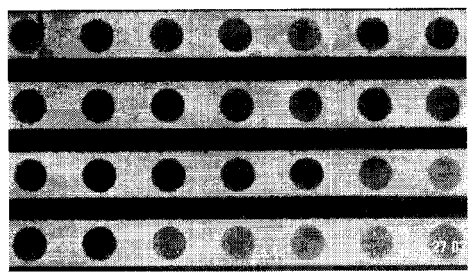
FIGS. 4(a) to (d) show reaction cells obtained experimentally that show that the intensity of the silver deposits increases with increasing concentration of the target DNA in the sample.
Figure 4B:
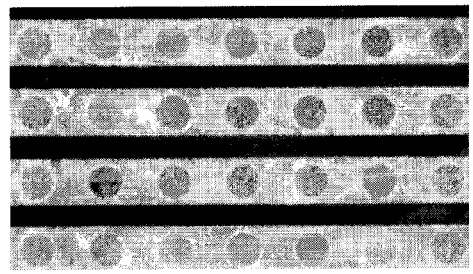
Figure 4C:
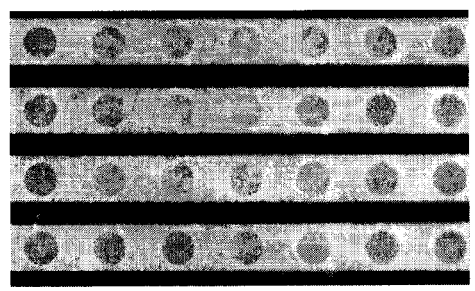
Figure 4D:
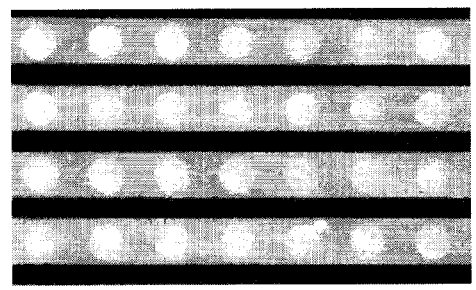

FIGS. 4(a)-(d) further demonstrate the effectiveness of the present invention by demonstrating that the silver deposits become darker with increasing target DNA concentration and thus that the optical signal increases in proportion to the target DNA concentration. FIGS. 4(a)-(c) show the chip after hybridization and detection with (a) undiluted target DNA, (b) target DNA diluted 5-fold, and (c) target DNA diluted 10-fold. It will be observed that the reaction cells in FIG. 4(a) are darker than those in FIG. 4(b) which in turn are darker than those in FIG. 4(c). FIG. 4(d) for comparison shows the chip with no target DNA present and thus white reaction cells with no silver deposited.

Figure 5:
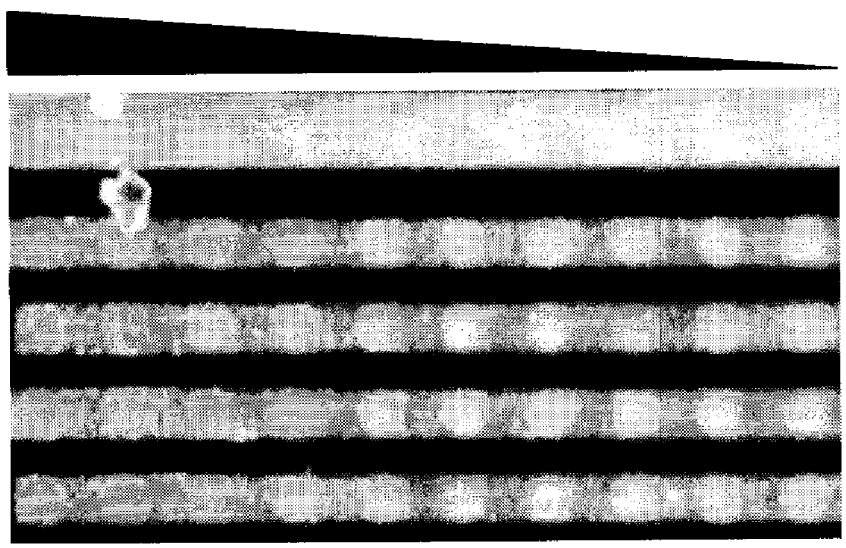
FIG. 5 shows reaction cells obtained experimentally that show that the intensity of the silver deposits varies with the concentration of the capture probe.

Finally, FIG. 5 shows that the intensity of the optical signal varies with the concentration of the DIG-capture probe. In FIG. 5 the DIG-capture probe concentration varies decreases from left to right and the reaction cells become correspondingly lighter as less silver is deposited.

The invention claimed is:

1. A DNA chip for detecting target DNA in a sample using electrical hybridization, comprising a substrate including at least one reaction cell, said at least one reaction cell having an aluminum oxide layer with a surface on which a DNA capture probe is attachable, and means for in-use electrically assisted hybridization between said target and said capture probe.

2. A DNA chip as claimed in claim 1, wherein hybridization between the target DNA and the capture probe is accelerated by the use of electric current.

3. A DNA chip as claimed in claim 2 wherein the electric current is a pulsed electric current.

* * * * *